United States Patent
Wang et al.

(10) Patent No.: US 12,121,217 B2
(45) Date of Patent: Oct. 22, 2024

(54) ENDOSCOPE AND OPERATING ARM

(71) Applicant: Shenzhen Edge Medical CO., Ltd., Shenzhen (CN)

(72) Inventors: Jianchen Wang, Shenzhen (CN); Yuanqian Gao, Shenzhen (CN); Zhimin Han, Shenzhen (CN); Linna Li, Shenzhen (CN)

(73) Assignee: Shenzhen Edge Medical CO., Ltd., Shenzhen (CN)

( * ) Notice: Subject to any disclaimer, the term of this patent is extended or adjusted under 35 U.S.C. 154(b) by 745 days.

(21) Appl. No.: 17/206,801

(22) Filed: Mar. 19, 2021

(65) Prior Publication Data

US 2021/0235977 A1 Aug. 5, 2021

Related U.S. Application Data (63) Continuation-in-part of application No. PCT/CN2019/106767, filed on Sep. 19, 2019.

(30) Foreign Application Priority Data

Sep. 20, 2018 (CN) .......................... 201811100002.2

(51) Int. Cl.
| | | |
|---|---|---|
| *A61B 1/05* | (2006.01) | |
| *A61B 1/00* | (2006.01) | |
| *A61B 1/045* | (2006.01) | |
| *A61B 34/37* | (2016.01) | |
| *A61B 34/30* | (2016.01) | |

(52) U.S. Cl.
CPC ............ *A61B 1/05* (2013.01); *A61B 1/00149* (2013.01); *A61B 1/00183* (2013.01); *A61B 1/045* (2013.01); *A61B 34/37* (2016.02); *A61B 2034/301* (2016.02)

(58) Field of Classification Search
CPC ... A61B 1/0149; A61B 1/00183; A61B 1/045; A61B 1/05; A61B 1/051
See application file for complete search history.

(56) References Cited

U.S. PATENT DOCUMENTS

| | | | |
|---|---|---|---|
| 2014/0343358 A1* | 11/2014 | Hameed | A61B 1/00183 |
| | | | 600/109 |
| 2016/0259159 A1* | 9/2016 | Matsui | A61B 1/045 |
| 2019/0216300 A1* | 7/2019 | Levy | A61B 1/00183 |

FOREIGN PATENT DOCUMENTS

| | | |
|---|---|---|
| CN | 102973317 A | 3/2013 |
| CN | 105764402 A | 7/2016 |
| CN | 206355022 U | 7/2017 |
| CN | 207168477 U | 4/2018 |
| CN | 108542335 A | 9/2018 |
| CN | 207822491 U | 9/2018 |
| CN | 109222860 A | 1/2019 |
| CN | 109222861 A | 1/2019 |

(Continued)

*Primary Examiner* — Aaron B Fairchild
(74) *Attorney, Agent, or Firm* — ScienBiziP, P.C.

(57) ABSTRACT

The application discloses an endoscope and an operating arm. The endoscope includes two camera units and a driving portion. The camera units are configured to obtain images. Optical axes of the two camera units can intersect. The driving portion is connected to the two camera units for driving at least one camera unit to move, thereby changing an angle between the optical axes of the two camera units. The endoscope is capable of being adjusted as needed, and the application range is wide.

11 Claims, 7 Drawing Sheets

(56) References Cited

FOREIGN PATENT DOCUMENTS

| CN | 109222862 A | 1/2019 |
|---|---|---|
| CN | 109222863 A | 1/2019 |

\* cited by examiner

ENDOSCOPE AND OPERATING ARM

FIELD

The subject matter herein generally relates to surgical systems, in particular to an endoscope and an operating arm.

BACKGROUND

Minimally invasive surgery refers to a surgical method of performing a procedure in a human body cavity using modern medical instruments and related devices such as laparoscopes, thoracoscopes, and the like. Compared with the traditional surgery mode, minimally invasive surgery brings the benefits of minimal trauma, causes less pain, faster recovery, and other benefits.

With advances in science and technology, minimally invasive surgical robot technologies are increasingly mature and widely used. At present, however, the endoscope used in very localized procedures is not capable of the full adjustment and manipulation as it should have, and the application range of the endoscope is limited.

SUMMARY

The present disclosure provides an endoscope capable of more extensive adjustment and an operating arm supporting and manipulating the endoscope.

An endoscope includes two camera units and a driving portion. Optical axes of the two camera units intersecting. The driving portion is connected to the two camera units, and is configured for driving at least one of the two camera units to move, thereby changing an angle between the optical axes of the two camera units.

In one embodiment, the driving portion includes a driving unit moving linearly to drive the at least one of the two camera units to rotate, to change the angle between the optical axes of the two camera units.

In one embodiment, the driving portion includes another connecting rod, wherein one end of each connecting rod is connected to the driving unit and other end of each connecting rod is connected to a corresponding one of the camera units.

In one embodiment, the endoscope further includes a shell, wherein the camera units and the driving portion are arranged in the shell, the shell defines a rotation shaft, and each of the camera units is rotatable mounted to the rotation shaft.

In one embodiment, velocity of angular changes of the two camera units are the same when the two camera units are adjusted.

In one embodiment, velocities of angular changes of the two camera units are different when the two camera units are adjusted.

In one embodiment, the two camera units are both driven by the driving portion.

In one embodiment, one of the two camera units is driven by the driving portion and the position of the other one of the two camera units is unchanged.

In one embodiment, the driving portion drives the two camera units to move simultaneously.

In one embodiment, the driving portion drives each camera unit to adjust the optical axis of each camera unit.

In one embodiment, the endoscope includes at least three camera units, wherein the optical axes of two of the camera units intersect.

In one embodiment, the endoscope includes four camera units, the four camera units are divided into two groups, and each group of the camera units includes two camera units of which optical axes intersect; and the point of the intersection of the optical axes of each group is located in different spaces.

In one embodiment, the optical axis of each camera unit is the same as the extending direction of the shell of the camera unit.

In one embodiment, an angle is formed between the optical axis of the camera unit and the extending direction of the shell of the camera unit.

In one embodiment, the camera unit further includes a stabilizing portion. The stabilizing portion includes a plurality of elastic members located between the two camera units, or the plurality of elastic members can be located between the shell of the endoscope and the two camera units.

An operating arm includes the endoscope.

A slave operating device includes the operating arm and a mechanical arm. The operating arm is disposed on the mechanical arm.

A slave operating device include a master console and the slave operating device. The slave operating device is configured to perform the corresponding operation in response to control commands sent by the master console.

BRIEF DESCRIPTION OF THE DRAWINGS

To describe the technical solutions in the embodiments of the present disclosure or in the prior art more clearly, the following briefly introduces the accompanying drawings required for describing the embodiments. The accompanying drawings and the following descriptions show merely some embodiments of the present invention, and a person of ordinary skill in the art may still derive other drawings from these accompanying drawings without creative efforts.

DETAILED DESCRIPTION

Implementations of the disclosure will now be described, by way of embodiments only, with reference to the drawing. The disclosure is illustrative only, and changes may be made in the detail within the principles of the present disclosure. It will, therefore, be appreciated that the embodiments may be modified within the scope of the claims.

The present application makes reference to the associated drawings. Preferred embodiments of the present application are set forth in the accompanying drawings. This application may, however, be embodied in many different forms and is not limited to the embodiments described herein. Rather, these embodiments are provided for the purpose of providing a more thorough and thorough understanding of the disclosure of the present application.

It should be noted that when an element is referred to as being "disposed on" another element, it may be directly on the other element or intervening elements may also be present. When an element is considered to be "connected" to another element, it may be directly connected to another element or intervening elements may be present at the same time. When an element is considered to be "coupled" to another element, it may be directly coupled to another element or intervening elements may be present at the same time. As used herein, the terms "vertical", "horizontal", "left", "right" and the like are intended for purposes of illustration only and are not intended to be limiting. As used herein, the terms "distal end" and "proximal end" are common terms in the art of interventional medical devices, where "distal end" refers to the end farthest away from the operator during the surgical procedure, and the "proximal end" refers to the end closest to the operator during the surgical procedure. Unless defined otherwise, all technical and scientific terms used herein have the same meaning as commonly understood by one of ordinary skill in the art. The terminology used herein is for the purpose of describing particular embodiments only and is not intended to be limiting. As used herein, the term "and/or" includes all combinations of one or more of the associated listed items.

Figure 1:
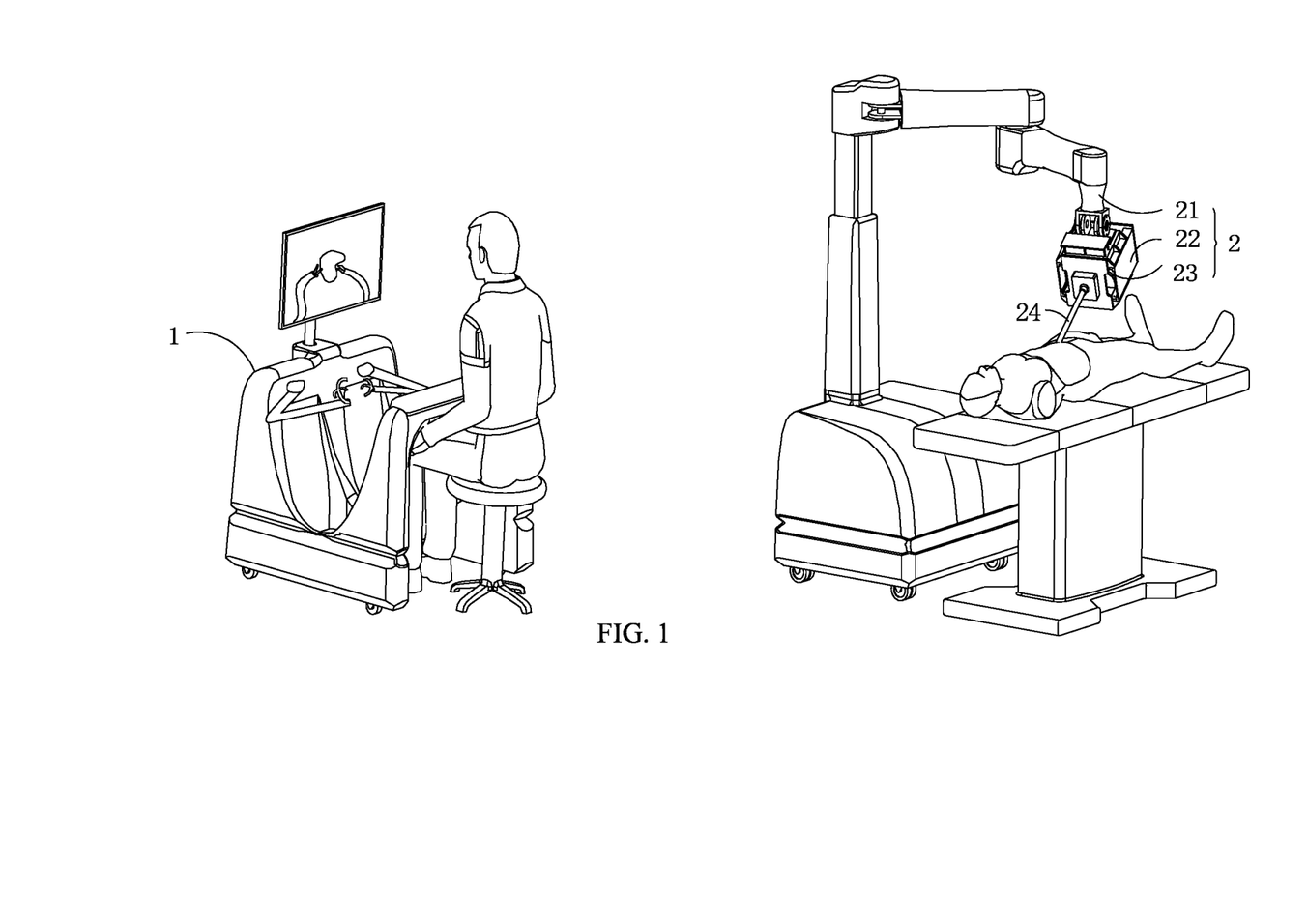
FIG. 1 is a structural schematic view of an embodiment of a surgical robot according to the present disclosure.
Figure 2:
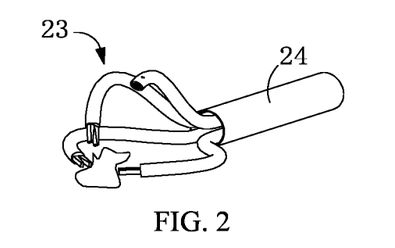
FIG. 2 is a partial schematic view of an embodiment of a slave operating device.
Figure 3:
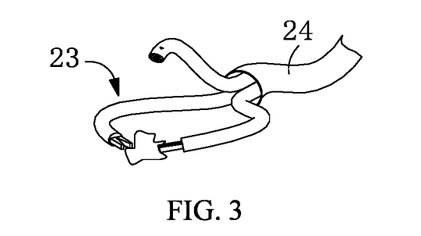
FIG. 3 is a partial schematic view of an embodiment of a slave operating device.

As shown in FIGS. 1-3, an embodiment of a surgical robot of the present application and different embodiments of the slave operating device are shown.

The surgical robot includes a master console 1 and a slave operating device 2. Wherein the master console 1 is used for sending control commands to the slave operating device 2 according to the commands of the surgeon to control the slave operating device 2. The master console 1 is also used for displaying images acquired from the slave operating device 2. The slave operating device 2 is used for responding to the control commands sent by the master console 1 and performing corresponding operations, and the slave operating device 2000 is also used for acquiring images in the human body.

Specifically, the slave operating device 2 includes a mechanical arm 21, a power mechanism 22 disposed on the mechanical arm 21, an operating arm 23 disposed on the power mechanism 22, and a sleeve 24 sleeving the operating arm 23. The mechanical arm 21 is used for adjusting the position of the operating arm 23. The power mechanism 22 is used for driving the operating arm 23 to perform an operation. The operating arm 23 can enter and extend into the human body and perform a surgical operation by the end effector 31 located at the distal end of the operating arm, and/or acquiring images within the human body. Wherein the end effector is an electric knife, a clamp, or part of an endoscope. As shown in FIG. 2 and FIG. 3, the operating arm 23 passes through the sleeve 24, and the end effector 31 extends out of the sleeve 24 and is driven by the power mechanism 22 to perform the operation. In FIG. 2, the part of the operating arm 23 located in the sleeve 24 is rigid. In FIG. 3, the part of the operating arm 23 located in the sleeve 24 is flexible, and the sleeve can flex with the flexible part. In another embodiment, the sleeve 24 may also be omitted, at which point the sleeve is not required.

As shown in FIGS. 4 to 12, an embodiment of the operating arm with the endoscope and schematic views of different embodiments of the endoscope are shown.

Figure 4:
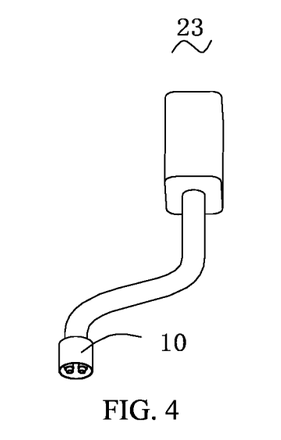
FIG. 4 is a partial schematic view of an embodiment of an endoscope.

The endoscope 10 includes a shell 100, two camera units 200, and a driving portion 300. Wherein the two camera units 200 and the driving portion 300 are located in the shell 100. The camera units are used for obtaining images and the optical axes of the two camera units intersect. The driving portion 300 is connected to the camera units 200 and drives at least one of the camera units to move, thereby changing the angle between the optical axes of the two camera units 200. In another embodiment, the shell 100 of the endoscope 10 may also be omitted.

There are a variety of driving relationships between the driving portion 300 and the camera units 200. For example, the driving portion 300 can drive the two camera units 200 to move simultaneously. As another example, there can be two driving portions 300 and the two driving portions 300 drive the two camera units 200 to move independently. As another example, the driving portion 300 just drives one camera unit 200 to move and the other camera unit 200 is not moved.

The two camera units 200, driven by the driving portion 300, may move synchronously or non-synchronously. When the two camera units 200 move non-synchronously, the two camera units 200 are capable of being adjusted individually. One camera unit 200 can be adjusted and the other one not affected. For example, one driving portion 300 can drive two camera units 200 to move. As another example, two driving portion 300 can drive two camera units to move synchronously. As another example, two driving portions 300 can drive two camera units to move, but non-synchronously.

It is noted that, velocity of angular changes of two adjusted camera units 200 may be the same or may be different. For example, the velocity of angular changes of the two camera units 200 which moves synchronously, are the same. As another example, the velocity of angular changes of the two camera units 200 which moves non-synchronously, are the same. As another example, the velocity of angular changes of the two camera units 200 which move synchronously can be different.

Figure 5:
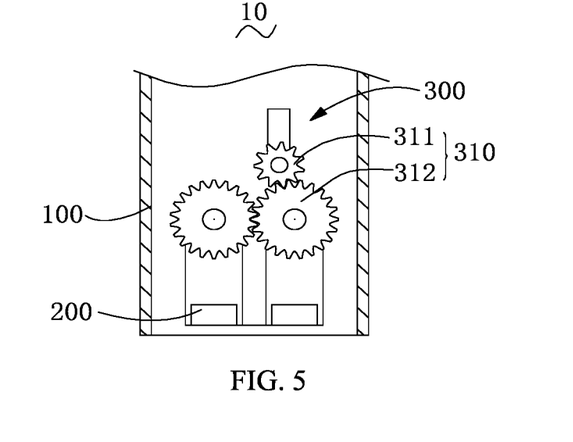
FIG. 5 is a partial schematic view of an embodiment of an endoscope.
Figure 6:
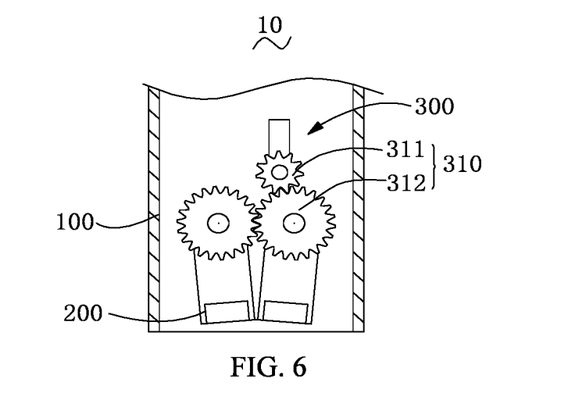
FIG. 6 is another partial schematic view of the endoscope shown in FIG. 5.

In one embodiment, the driving portion 300 rotates to drive the camera unit 200 to rotate, thereby changing the angle between the optical axes of the two camera units 200. As FIGS. 5 and 6 shown, the driving portion 300 includes a gear assembly 310, connected to the camera unit 200, for driving the camera unit 200 connected to the gear assembly 310. Wherein the gear assembly 310 includes a drive gear 311 and at least two driven gears 312. The two driven gears 312 are connected to the two camera units 200. The drive gear 311 drives the two driven gears 312 to rotate. Specifically, the two driven gears engage with each other. The drive gear 311 can engage with one driven gear 312, thereby enabling the two camera units 200 to move towards or away from each other. In one embodiment, the two driven gears are the same. In another embodiment, the two driven gears are different.

In one embodiment, the gear assembly 310 may also include two drive gears 311 connected to the two driven gear 312 for adjusting the two driven gears. The two driven gears can be adjusted synchronously or non-synchronously.

In one embodiment, the drive gear 311 engages with the two driven gears 312. For example, there are three driven gears 312. Two driven gears 312 are connected to the two camera units 200, and the other driven gear 312 and the drive gear 311 are located between the two driven gears 312 described above. The four gears can engage with each other in turn, thereby enabling the two camera units 200 to move towards or away from each other. As another example, there are two driven gears 312, and the drive gear 311 is located between the two driven gears 312 and engages with both of the two driven gears 312.

It is noted that, in another embodiment, the number of driven gears 312 and/or the drive gears 311 may vary as needed for adjusting the camera units 200. For example, only one camera unit 200 may need to be adjusted. For this circumstance, the corresponding gears connected to the other camera unit 200 may be omitted. In addition, the sizes of the gears can be selected as needed for adjusting the speed of motion of the camera units 200.

In one embodiment, the driving portion 300 may move linearly to drive the camera unit 200 to rotate, thereby changing the angle of the optical axes of the two camera units 200. The driving portion 300 moving linearly to drive the camera unit 200 means that at least a main driving part of the driving portion 30 moves linearly.

Figure 7:
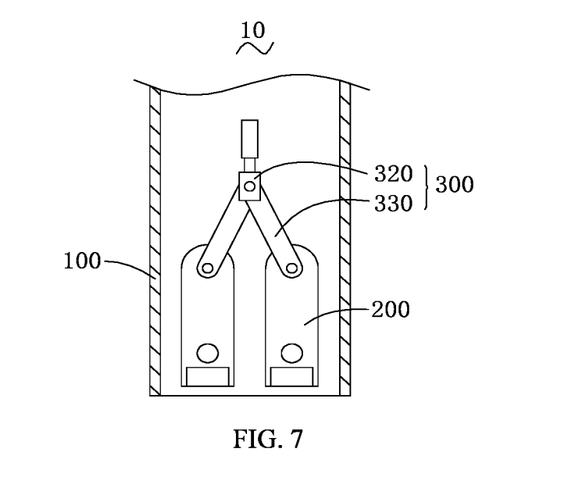
FIG. 7 is a partial schematic view of an embodiment of an endoscope.
Figure 8:
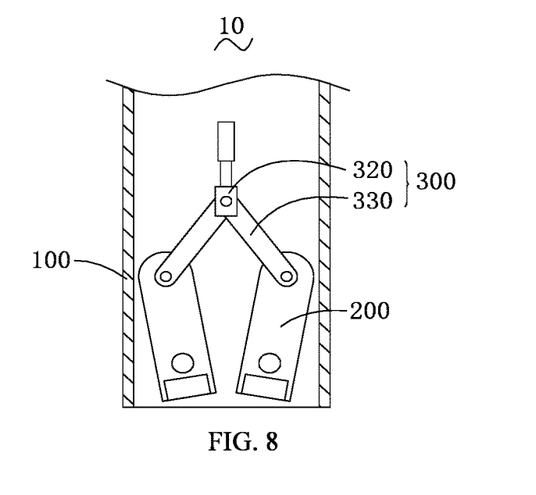
FIG. 8 is another partial schematic view of the endoscope shown in FIG. 7.

In the embodiment shown in FIGS. 7 and 8, the driving portion 300 includes a driving unit 320 and a connecting rod 330 connected to the driving unit 320. The drive unit 320 is configured to move linearly. One end of the connecting rod 330 is connected to the drive unit 320 and another end of the connecting rod 330 is connected to the camera unit 200. The drive 320 moves linearly to drive the connecting rod 330 to swing, thereby driving the camera unit 200 connected to the connecting rod 330 to move to adjust the position of the camera unit 200. In one embodiment, there are two connecting rod 330 connected to the two camera units 200. One end of each connecting rod 330 is rotatably connected to the driving unit 320, and the other end of each connecting rod 330 is rotatably connected to the camera unit 200. Specifically, the shell 100 includes a rotating shaft and the camera units 200 are rotatably mounted to the rotating shaft. The camera units 200 rotate about the rotating shaft when the camera units 200 are driven by the connecting rod 330.

In one embodiment, there are two driving units 320 and each driving unit 320 is connected to one connecting rod 330 for driving the camera unit 200 individually. In one embodiment, only one camera unit 200 is connected to the driving portion 300. At this point, only one driving unit 320 and one connecting rod 330 are needed for connecting to the camera unit 200.

In one embodiment as shown in FIGS. 9 to 12, the driving portion 300 includes a driving unit 320 slidably connected to the camera unit 20 for changing the angle between the optical axes of the two camera units 200. The driving portion 320 can move linearly to drive the camera unit 200 to rotate.

Specifically, a guiding rail 210, corresponding to the driving unit 320, is disposed on each of the two camera units 200. The driving unit 320 slides along the guiding rails 210 to drive the camera unit 200 to move. The guiding rail 210 may be a slot structure or a protruding structure. The driving unit 320 is connected to the guiding rail 210. The slot structure is a through slot or a blind slot. For example, the guiding rail 210 is a slot structure and the driving portion 320 includes a sliding member with a protrusion. The sliding member is capable of sliding in the slot structure. As another example, as in embodiment shown in FIG. 9, the guiding rail 210 is a slot, and the driving portion 320 includes a sliding wheel 321 received in the slot. The sliding wheel 321 is capable of moving along the slot.

Figure 9:
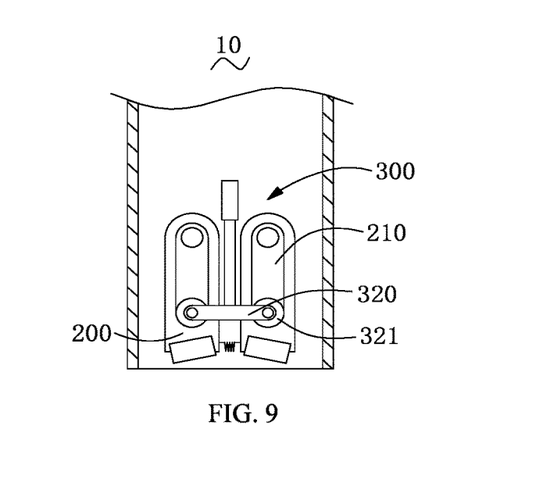
FIG. 9 is a partial schematic view of an embodiment of an endoscope.
Figure 10:
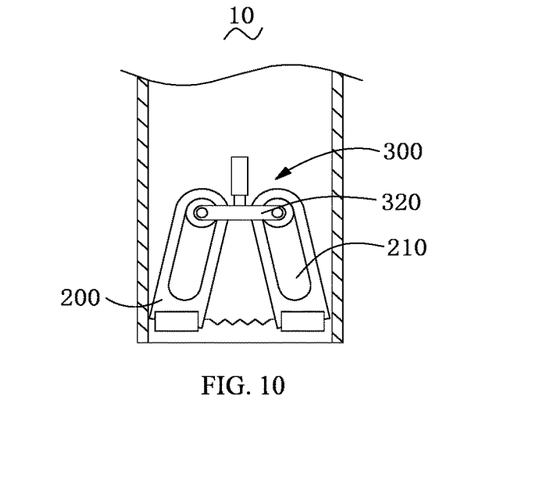
FIG. 10 is another partial schematic view of the endoscope shown in FIG. 9.
Figure 11:
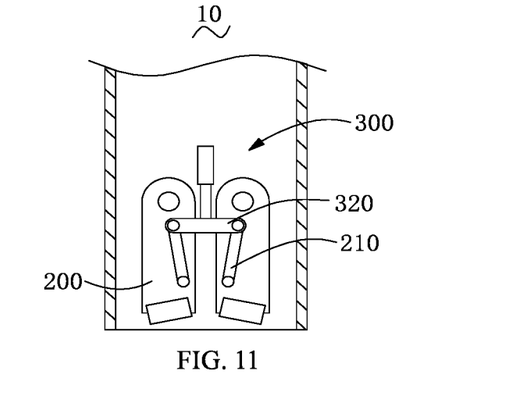
FIG. 11 is a partial schematic view of an embodiment of an endoscope.
Figure 12:
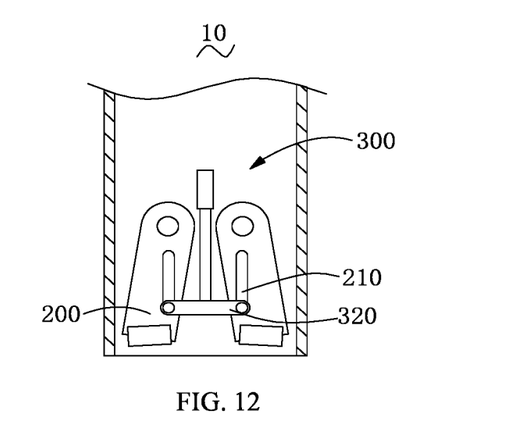
FIG. 12 is another partial schematic view of the endoscope shown in FIG. 11.

In the embodiment, a guiding rail 210 is disposed on each camera unit 200 and is slidably connected to the driving unit 320. Wherein the driving unit 320 is slidably connected to the two guiding rails 210. Specifically, there is one driving unit 320 and two end portions of the driving unit 320 are slidably connected to the two guiding rails 210 disposed on the two camera units 200 respectively. When the driving unit 320 moves linearly, the two end portions drive the two camera units to rotate via the guiding rails 210. In another embodiment, there are two driving unit 320 each driving one camera unit 200.

In one embodiment, there is an angle between the movement direction of the part of the driving unit 320 connected to the guiding rail 210 and the guiding rail. For example, the end portions of the driving unit are connected to the guiding rail, and there is an angle between the movement of the end portion of the driving unit 320 and the guiding rail 210. The end portion is slidably connected to the guiding rail. When the driving unit 320 moves linearly, the driving unit 320 pushes the camera unit 200 to rotate via the guiding rail 210 because of the angle between the movement direction of the end portion and the guiding rail 210. The length of the driving unit 320 may or may not be variable. For example, there is an angle between the guiding rail and the movement direction of the end portion of the driving unit 320, and the driving unit 320 can be scaled for driving the camera unit 200.

The angle between the guiding rail 210 and the movement direction of the driving unit 320 can be set or adjusted in several ways. For example, in one embodiment shown in FIGS. 9 and 10, the guiding rail 210 is parallel to the extending direction of the camera unit 200. The driving portion 300 further includes an elastic portion located between the two camera units 200 for enabling the angle between the optical axes of the two camera units 200 to change against an elastic force when the driving unit 320 is located in different position of the guiding rail 210. As another example, the extending direction of the camera unit is parallel to the guiding rail, and an angle is formed between the extending direction of the camera unit and the movement direction of the driving unit.

The guiding rail is straight or curved as needed. For example, the guiding rail 210 in the embodiment is arc-shaped or S-shaped.

In addition, a limiting structure is disposed on the guiding rail 210 and is connected to the driving unit 320 for preventing the guiding rail 210 from being disconnected from the driving unit 320. For example, the guiding rail 210 is a slot and a side wall of the slot defines a limiting slot. The driving unit 320 is received in the slot and can abut the end of the limiting slot.

FIGS. 13 to 17 show different embodiments of an endoscope 10.

Figure 13:
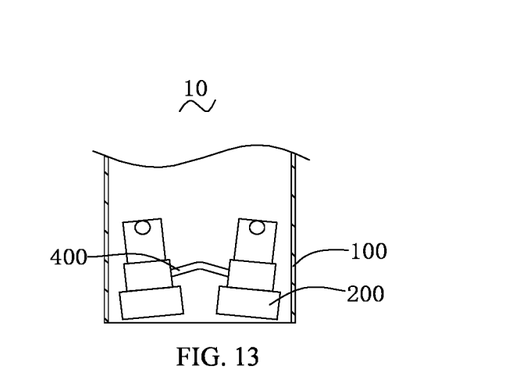
FIG. 13 is a partial schematic view of an embodiment of an endoscope.
Figure 14:
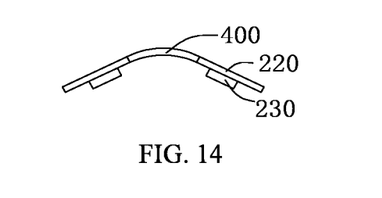
FIG. 14 is a partial schematic view of the endoscope shown in FIG. 13.

The endoscope 10 includes a first circuit board 400 and two camera units 200. Wherein the first circuit board 400 is a flexible circuit board. The camera units 200 includes a second circuit board 220 and sensor unit 230 disposed on the second circuit board 220. The two second circuit boards 220 are connected each other via the first circuit board 400 for communicating with each other. An angle is formed between the two second circuit boards 200 to enable the optical axes of the two camera units 200 to intersect.

It is noted that, the first circuit board 400 may extend into the shell 100 of the camera unit 200 to be connected to the second circuit board 220, or may be outside the shell 100 when connected to the second circuit board 220. At this point, the second circuit board 220 extends out of the shell 100 of the camera unit 200.

The endoscope 10 enables the optical axes of the two camera units 200 to intersect via the first circuit board 400. The structure of the endoscope 10 is simple and is convenient to manufacture. The angle between the two optical axes can be adjusted via the first circuit board 400, which enables a wide application range of the endoscope.

In one embodiment, the second circuit board 220 is a flexible circuit board. For example, the second circuit board 220 and the first circuit board 400 are integrated. In another embodiment, the second circuit board 220 may be a rigid circuit board. At this point, the camera unit 200 is more stably connected to the second circuit board. Alternatively, one of the two second circuit boards 220 is a rigid circuit board and the other one of the two second circuit boards 220 is a flexible circuit board.

In one embodiment, the first circuit board 400 is detachably connected to at least a part of the second circuit board 220. For example, the first circuit board 400 is detachably connected to the two second circuit boards 220. As another example, the first circuit board 400 is detachably connected to one of the two second circuit boards 220, and is permanently connected to the other one of the two second circuit boards 220. Specifically, the first circuit board 400 includes a first interface and the second circuit board 220 includes a second interface connected to the first interface. The distance or angle between the two second circuit boards 220 can be adjusted by replacing the first circuit board 400 with another one, and the optical axes of the two camera units 200 thus have further adjustability. In one embodiment, the first circuit board 400 includes two first interfaces respectively connected to two second interfaces of the two second circuit boards 220.

Figure 15:
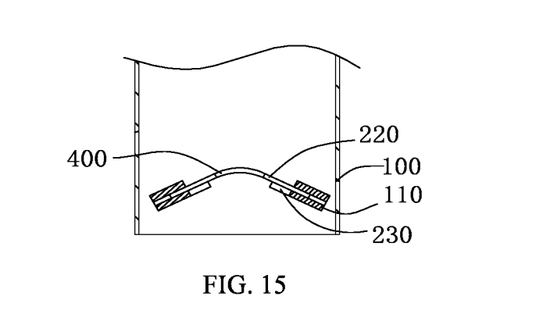
FIG. 15 is a partial schematic view of the endoscope shown in FIG. 13.
Figure 16:
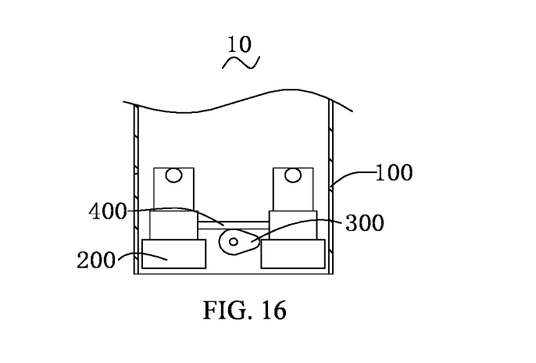
FIG. 16 is a partial schematic view of an embodiment of an endoscope.
Figure 17:
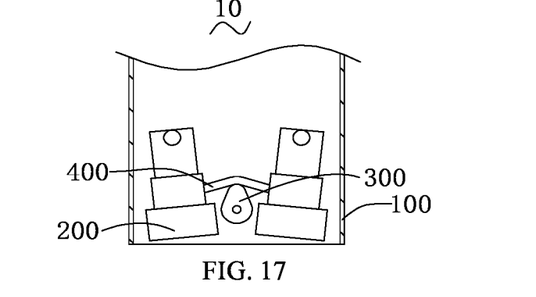
FIG. 17 is another partial schematic view of the endoscope shown in FIG. 16.

In one embodiment, the endoscope 10 includes a shell 100. The shell 100 includes a positioning structure 110. The two camera units 200 are positioned by the positioning structure 110. That is, the angle between the optical axes of the camera units 200 is fixed by the positioning structure 110. Fox example, in one embodiment as shown in FIG. 15, the positioning structure 110 is a positioning slot, and the second circuit boards are received in the positioning slot and resist against the positioning slot. The first circuit board 400 may be inserted in the positioning slot, or the first circuit board and the second circuit boards are inserted in the positioning slot. As another example, the positioning structure is a positioning slot and main bodies of the camera units 200 are received in the positioning slot. It is also understood that, the shells 100 of the camera units 200 are received in the positioning slot.

In one embodiment, the endoscope 10 further includes a driving portion 300 connected to the camera units 200 and/or the first circuit board 400, and the driving portion 300 drives at least one camera unit 200 to change the angle between the optical axes of the two camera units 200. It is also understood that, the driving portion 300 not only directly drives the camera unit 200 to move to change the optical axes, but also drives the camera unit 200 to move by driving the first circuit board 400 to move. Alternatively, the driving portion 300 moves the camera unit 200 and the first circuit board 400 synchronously.

There are several ways for the driving portion 300 to drive the first circuit board 400 to move. In one embodiment, the driving portion 300 moves linearly to drive the first circuit board 400 to change the degree of flex of the first circuit board 400. For example, the camera units 200 are rotatably connected to the shell 100. The driving portion resists against the first circuit board 400 during the driving process. The end portion of the driving portion 300 includes an arc surface. In one embodiment shown in FIGS. 16 and 17, the driving portion 300 rotates to move the first circuit board 400, thereby driving the camera units 200 to rotate. For example, the camera units 200 are rotatably connected to the shell 100. The driving portion 300 has the structure of a cam rotatably connected to the shell of the endoscope 10.

The embodiment of the driving portion 300 driving the camera units 200 may be the same as in the embodiments described above, and will not be repeated here.

In order to more stably adjust the camera units 200, a stabilizing portion may also be provided on the camera units 200. For example, the stabilizing portion can be elastic members disposed between the camera units 200 or between the camera units 200 and the shell 100 of the endoscope 10. As another example, a damping unit is disposed on the rotating shaft of the adjusting unit.

It is noted that, the endoscope 10 may also include as many camera units 200 as are needed. For example, the endoscope 10 includes three camera units 200 or four camera units 200. Wherein the optical axes of the plurality of camera units 200 can be arranged as needed. For example, the plurality of optical axes can intersect at a single point. As another example, two optical axes can intersect at a certain point and the other optical axes can intersect at another point or points. As another example, the endoscope 10 includes four camera units 200 divided into two pairs. Each pair includes two camera units 200 and the optical axes of two camera units 200 intersect. The intersection points of the two pairs are located in different spaces which enables the observer to obtain a view of multiple points or places.

In addition, in the above embodiment, the optical axes of the camera units are the same as the extending direction of the shell of the endoscope, or can form an angle with the extending direction of the shell.

It is noted that, the endoscope of the present disclosure may be applied to the operating arm of the surgical robot or other devices where the placement of the endoscope is desired.

The various technical features of the above-described embodiments may be combined in any combination, so long as the function remains precise, and all possible combinations of the various technical features in the above-described embodiments are included. However, as long as the combination of these technical features does not conflict, it is to be understood that the scope of the present specification is not to be taken in a limiting sense.

The above-described embodiments have only expressed several embodiments of the present application, which are not to be construed as limiting the scope of the present application. It should be noted that variations and modifications may be made to one of ordinary skill in the art without departing from the spirit of the present application, all of which fall within the scope of the present application. Therefore, the scope of the appended claims should be accorded the broadest interpretation so as to encompass all such modifications and similar arrangements.

What is claimed is:

1. An endoscope, comprising:
   two camera units for obtaining images, optical axes of the two camera units intersecting;
   a driving portion connected to the each of two camera units, the driving portion being configured for driving at least one of the two camera units to rotate, thereby changing an angle between the optical axes of the two camera units;
   a shell, wherein the camera units and the driving portion are received in the shell, the at least one of the camera units is rotatably mounted to the shell for being adjusted, the driving portion is configured to drive the at least one of the camera units to rotate; and
   a first circuit board, and the first circuit board being a flexible circuit board;
   each of the camera units comprising a second circuit board and a sensor unit mounted on the second circuit board, wherein the second circuit boards of the two camera units are connected to each other via the first circuit board.

2. The endoscope of claim 1, wherein the driving portion is a cam mechanism, the driving portion is rotatably mounted to the shell and is configured to abut against the first circuit board and rotatable to change a bending degree of the first circuit board thereby driving the two camera units to rotate.

3. The endoscope of claim 1, wherein the two camera units are rotatably mounted to the shell; the driving portion comprises a gear assembly; the gear assembly comprises a driving gear and two driven gears; the two driven gears are connected to the two camera units respectively; and the driving gear is configured to drive a corresponding one of the two driven gears to rotate thereby driving the two camera units to rotate.

4. The endoscope of claim 1, wherein the two camera units are rotatably mounted to the shell; the driving portion comprises a driving unit and two connecting rods; first ends of the two connecting rods are rotatably connected to the two camera units respectively, and second ends of the two connecting rods are each connected to the driving unit; and the driving unit is linearly movable to drive the two connecting rods to swing, thereby driving the two camera units to rotate.

5. The endoscope of claim 1,
   wherein the two camera units are rotatably mounted to the shell; a guiding rail is disposed on each of the two camera units; the driving portion comprises a driving unit, and a connecting rob is connected to a bottom portion of the driving unit; the driving unit is connected to the two guiding rails respectively via two end portions of the connecting rod, and is linearly movable to drive the two camera units to rotate;
   wherein an extending direction of the guiding rail is the same as an extending direction of the camera unit on which the guiding rail is disposed; first ends of the two camera units are rotatably connected to the shell, and second ends of the two camera units are connected to each other via an elastic member; an angle between optical axes of the two camera units changes when the driving unit is on the guiding rails at different positions; or an angle is formed between an extending direction of the guiding rail and an extending direction of the camera unit on which the guiding rail is disposed.

6. The endoscope of claim 1, wherein one of the two camera units is rotatably mounted to the shell and the other one of the two camera units is securely mounted to the shell, and the driving portion abuts against the first circuit board and is movable linearly to change a bending degree of the first circuit board thereby driving the one of the two camera to rotate; or the driving portion is a cam mechanism, the driving portion is rotatably mounted to the shell and is configured to abut against the first circuit board and rotate to change a bending degree of the first circuit board to drive the two camera units to rotate.

7. The endoscope of claim 1, wherein one of the two camera units is rotatably mounted to the shell and the other one of the two camera units is securely mounted to the shell; the driving portion comprises a gear assembly; the gear assembly comprises a driving gear and a driven gear; the driven gear is connected to the one of the two camera units; the driving gear engages with the driven gear to rotate to drive the camera unit connected to the driven gear to rotate.

8. The endoscope of claim 1, wherein one of the two camera units is rotatably mounted to the shell and the other one of the two camera units is securely mounted to the shell; the driving portion comprises a driving unit and a connecting rod; one end of the connecting rod is rotatably connected to the two camera units, and another end of the connecting rod is connected to the driving unit; and the driving unit is configured to linearly move to drive the connecting rod to swing, thereby driving the two camera units to rotate.

9. The endoscope of claim 1, wherein one of the two camera units is rotatably mounted to the shell and the other one of the two camera units is securely mounted to the shell; the driving portion comprises a driving unit and a connecting rod; one end of the connecting rod is rotatably connected to the two camera units, and another end of the connecting rod is connected to the driving unit; and the driving unit is configured to linearly move to drive the connecting rod to swing, thereby driving the two camera units to rotate.

10. The endoscope of claim 1, further comprising another camera unit, wherein optical axes of at least two of the three camera units intersect.

11. The endoscope of claim 10, wherein a number of the camera units is four, and the four camera units are divided into two groups; each group of the camera units comprises two camera units of which optical axes intersect.

* * * * *